(12) United States Patent
Cenko et al.

(10) Patent No.: US 8,937,723 B2
(45) Date of Patent: Jan. 20, 2015

(54) APPARATUS AND METHODS FOR OPTICAL COHERENCE TOMOGRAPHY AND CONFOCAL MICROSCOPY

(75) Inventors: Andrew T. Cenko, Waterloo (CA); Jeffrey T. Meade, Arden (CA); Arsen R. Hajian, Waterloo (CA); Jae K. Kim, Thunder Bay (CA)

(73) Assignee: Thunder Bay Regional Research Institute, Thunder Bay, ON (CA)

( * ) Notice: Subject to any disclaimer, the term of this patent is extended or adjusted under 35 U.S.C. 154(b) by 293 days.

(21) Appl. No.: 13/499,808

(22) PCT Filed: Oct. 1, 2010

(86) PCT No.: PCT/CA2010/001598
§ 371 (c)(1),
(2), (4) Date: May 11, 2012

(87) PCT Pub. No.: WO2011/091502
PCT Pub. Date: Aug. 4, 2011

(65) Prior Publication Data
US 2012/0218558 A1    Aug. 30, 2012

Related U.S. Application Data

(60) Provisional application No. 61/247,753, filed on Oct. 1, 2009.

(51) Int. Cl.
*G01B 9/02* (2006.01)
*G02B 3/02* (2006.01)
(Continued)

(52) U.S. Cl.
CPC .......... *G01N 21/4795* (2013.01); *A61B 5/0066* (2013.01); *G02B 27/283* (2013.01); *G01B 9/02056* (2013.01); *G01B 9/02091* (2013.01)

USPC .......................... 356/479; 359/709; 356/491

(58) Field of Classification Search
CPC ........... G01B 9/02091; G01B 9/02056; A61B 5/0066; A61B 5/0068; A61B 5/0073; A61B 3/102; A61B 3/1025; G01N 21/4795; G01N 2021/1787; G02B 5/001
USPC .......................... 356/479, 497, 491; 359/709
See application file for complete search history.

(56) References Cited

U.S. PATENT DOCUMENTS 4,541,280 A * 9/1985 Cielo et al. ...................... 73/603
5,285,223 A * 2/1994 Ueno et al. .................... 351/208
(Continued)

FOREIGN PATENT DOCUMENTS

EP    1887312 A1    2/2008

OTHER PUBLICATIONS

I. Golub and R. Tremblay, "Light focusing and guiding by an axicon-pair-generated tubular light beam", J. Opt. Soc. Am. B, vol. 7, No. 7, Jul. 1990.*
(Continued)

*Primary Examiner* — Kara E Geisel
*Assistant Examiner* — Violeta A Prieto
(74) *Attorney, Agent, or Firm* — Lynn C. Schumacher; Stephen W. Leonard; Hill & Schumacher

(57) ABSTRACT

An optical imaging device which receives an optical collimated input beam, the device having a pair of axicon lenses through which a beam is directed to generate a collimated ring beam, wherein the ring beam is scattered from a substance to generate a return beam, and to bypass a reflector that redirects the return beam to prevent the return beam from interfering with the input beam; and a detector which detects an image projected by the return beam.

15 Claims, 7 Drawing Sheets

(51) Int. Cl.
*G01N 21/47* (2006.01)
*A61B 5/00* (2006.01)
*G02B 27/28* (2006.01)

(56) References Cited

U.S. PATENT DOCUMENTS

| | | | |
|---|---|---|---|
| 2005/0018200 A1* | 1/2005 | Guillermo et al. | 356/479 |
| 2005/0206905 A1* | 9/2005 | Iwamoto et al. | 356/494 |
| 2006/0063989 A1* | 3/2006 | Hogan | 600/316 |
| 2007/0035742 A1* | 2/2007 | Hill | 356/493 |
| 2007/0205378 A1* | 9/2007 | Tomioka et al. | 250/458.1 |
| 2008/0266576 A1* | 10/2008 | Iwamoto | 356/614 |
| 2009/0128824 A1 | 5/2009 | Leitgeb et al. | |

OTHER PUBLICATIONS

M. Rioux, R. Tremblay, and P. A. Belanger, "Linear, annular, and radial focusing with axicons and applications to laser machining", Applied Optics, vol. 17, No. 10, May 15, 1978.*

L. M. Cabali'n and J. J. Laserna, "Atomic emission spectroscopy of laser-induced plasmas generated with an annular-shaped laser beam", J. Anal. At. Spectrom., 2004, 19, 445-450.*

* cited by examiner

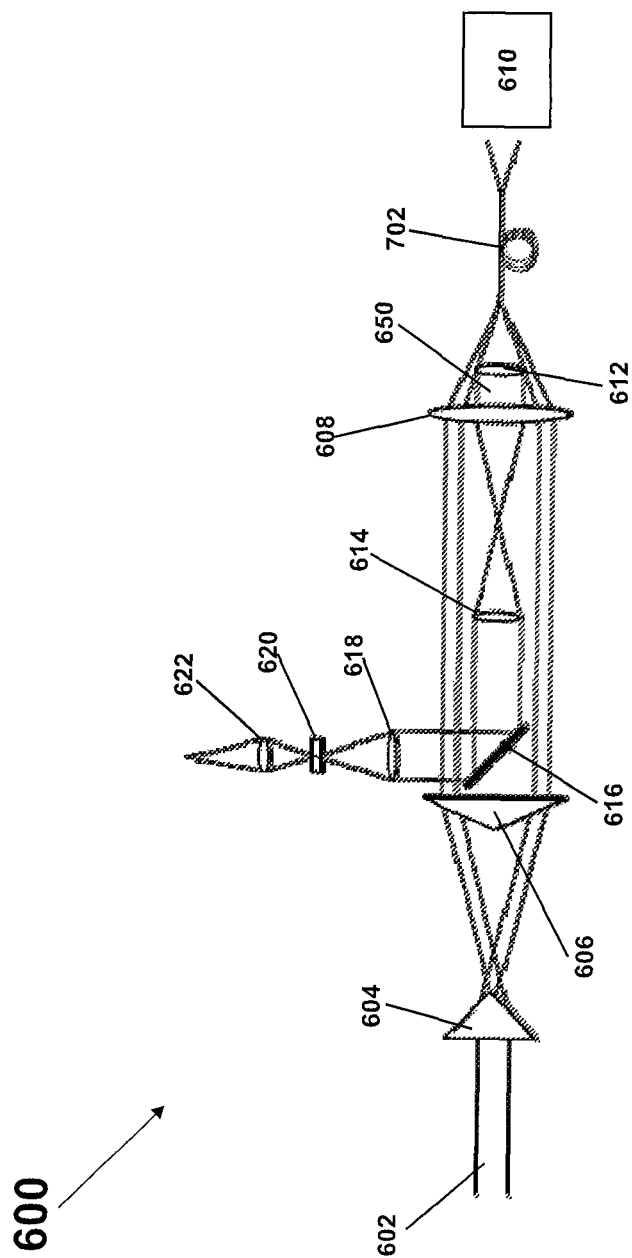

APPARATUS AND METHODS FOR OPTICAL COHERENCE TOMOGRAPHY AND CONFOCAL MICROSCOPY

RELATED APPLICATIONS

This application is a National Phase application claiming the benefit of PCT/CA2010/001598, titled "APPARATUS AND METHODS FOR OPTICAL COHERENCE TOMOGRAPHY AND CONFOCAL MICROSCOPY" filed on Oct. 1, 2010, in English, which further claims priority from U.S. Provisional Application No. 61/247,753 filed Oct. 1, 2009, the contents of which are herein incorporated herein by reference.

FIELD OF INVENTION

This invention relates to the field of optical scanning and more specifically relates to improved apparatus and methods for optical coherence tomography and confocal microscopy.

BACKGROUND

An optical source can be a cost-effective way of obtaining certain information from a substance by penetrating the surface, or surfaces, of a substance, and being subsequently scattered or reflected by the surface or surfaces. As described herein, surfaces includes interior surfaces within a substance. This scatter or reflection can be used to provide useful information with respect to the depth profile or physical structure of the surface. For example, certain medical imaging techniques can measure the reflectivity as a function of depth, and use this information to produce a three-dimensional image of a substance. To accurately measure the reflectivity, the scattered or reflected signal can be interfered with a reference beam, producing an output beam, that projects an interference pattern which is interpreted by an interferometer or other detector. These interference patterns are typically made up of multiple signal fringes and each signal fringe typically represents a depth of penetration value of the optical source into the substance. These multiple depth penetration values are used to generate a depth profile of the substance.

Optical coherence tomography (OCT) is one such imaging technique, used to obtain depth information of a substance. In OCT systems, light is typically split into a sample beam and a reference beam, the sample beam being projected onto the substance and being reflected or scattered off the surface or surfaces of the substance. The reflected or scattered beam is collimated to form a return beam, the return beam being interfered with the reference beam to generate an output beam, the output beam projecting an interference pattern onto an interferometer, for example, a CCD sensor, from which aspects of the structure of a substance can be obtained, for example the depth of various surfaces in the substance.

OCT systems generally fall into spectral domain and time domain systems. Time domain OCT (TDOCT) systems scan over a range of reference arm delays (often by moving a mirror) to allow for reconstruction of a depth profile. Spectral Domain OCT (SD OCT) systems examine the interference pattern as a function of wavelength (often by dispersing a broadband signal) as an alternative means of reconstructing the depth profile. The interference pattern as a function of wavelength can also be sampled by sweeping the wavelength of the light in the interferometer, often called Swept Source OCT (SSOCT). Theses reconstructed depth profiles can provide information on the structure of the examined substance.

Confocal imaging is a technique in which light outside of the imaging focal plane is not detected due to a pinhole located at the focal point in a conjugate focal plane. The resulting image is a thin slice of the sample object where the thickness is proportional to the diameter of the pinhole. Since out-of-plane light is generally disregarded, the image can be effectively de-blurred and the spatial resolution can be increased. A full three-dimensional image reconstruction can also be possible with a confocal system by imaging different slices independently and then stacking the slices in the appropriate order. Confocal systems are typically implemented as a microscope.

In each of OCT systems and confocal imaging systems, signal losses can occur due to the particular optical components used and their respective arrangement. For example, beam splitters can introduce losses. Typically, the beam splitter first splits the input beam forming a reference beam and a sample beam, the reference beam being the portion of the input beam reflected by the beam splitter and the sample beam being the portion transmitted through the beam splitter. The sample beam is projected onto a substance and is reflected or scattered off the surface, or surfaces, of the substance. This reflected or scattered beam is then collimated to form a return beam. The return beam projecting back to the same beam splitter, while the reference beam, originally generated by the beam splitter, is reflected back toward the same beam splitter by a reflective surface. The same beam splitter then can generate an output beam, the output beam being an interference beam generated by interfering the reference beam with the return beam by the same beam splitter reflecting a portion of the return beam and transmitting a portion of the reference beam through the beam splitter; however, losses in the signal occur due to a portion of the return beam being transmitted through the beam splitter, along with a portion of the reference beam being reflected by the beam splitter, these portions being directed back toward the input source. The beam portions directed back to the input source additionally interfere with the input source, causing signal losses in the output signal.

Some existing OCT and confocal imaging systems have boosted the optical power of the input beam to improve the resulting signal intensity of the resulting output signal. In such systems the same losses occur, but a desired intensity signal of the output beam intensity can be generated at a cost of additional energy due to the increased intensity of the input signal. Devices that provide improvements in output beam signal intensity can additionally provide an energy savings benefit, since an input beam of a lower signal intensity can produce an output beam of a desired signal intensity.

OCT and confocal imaging systems that avoid using optical elements in ways that generate signal losses, for example, using the same beam splitter to both split an input beam and generate an output beam, can reduce signal losses. OCT and confocal imaging systems using axicon lenses can use the axicon lens to bypass beam splitters and other optical elements, and in some embodiments replacing beam splitters, to reduce signal losses in the system and increase the total output signal intensity which can improve the quality of the system and can provide energy savings.

SUMMARY OF THE INVENTION

In an aspect of the present invention, an optical imaging device which receives an optical collimated input beam is provided, the device comprising a beam splitter which splits the input beam into a sample beam and a reference beam, wherein the sample beam is scattered from a substance to generate a return beam; a pair of axicon lenses through which at least one of the sample beam and the return beam is directed to bypass a reflector that redirects at least one of the input beam and the reference beam, to prevent either the return beam or the reference beam from interfering with the input beam; and a detector which detects an interference pattern of an output beam generated by interfering the reference beam with the return beam.

The optical imaging device may further comprise a focusing lens which focuses the sample beam onto a surface of the substance.

The optical imaging device may comprise a second beam splitter, wherein the reference beam and return beam may be split by the beam splitter to generate two output beams and may further comprise a mask with an aperture therethrough which may reducing the diameter of the reference beam such that it can be substantially similar to the diameter of the reference beam.

In alternative embodiments, the beam splitter may be a polarization beam splitter of the type that reflects two different types of polarized light (hereinafter referred to as type A and type B polarized light). In such embodiments, the input beam may comprise type A and type B polarized light and the reference beam may be generated by the beam splitter reflecting the type A polarized light. Additionally, in such embodiments, the sample beam may be generated by the beam splitter transmitting the type B polarized light.

In these alternative embodiments, the optical imaging device may further comprise a polarization element for receiving the return beam and may transform the return beam into type A polarized light, wherein the beam splitter may receive and may reflect the polarized return beam.

In some embodiments of the present invention, the optical imaging device may be an optical coherence tomography device.

In an additional aspect of the present invention, an optical imaging device which receives an optical collimated input beam is provided, the device comprising a pair of axicon lenses through which the input beam is directed to generate a collimated ring beam, wherein the ring beam is scattered from a substance to generate a return beam, and to bypass a reflector that redirects the return beam to prevent the return beam from interfering with the input beam; and a detector which detects an image projected by the return beam.

In some embodiments the optical imaging device may further comprise a focusing lens which may focus the sample beam onto a surface of the substance. The optical imaging device may additionally comprise a pin hole which may focus the sample beam. In some embodiments, the optical imaging device may be a confocal imaging microscope.

In a further aspect of the present invention, a method for detecting an interference pattern with an optical imaging device is provided, the method comprising dividing an input beam into a sample beam and a reference beam; scattering the sample beam from a substance to generate a return beam; passing at least one of the sample beam and the return beam through a pair of axicon lenses to bypass a reflector that redirects at least one of the input beam and the reference beam to prevent interference with the input beam by either the return beam or the reference beam; and interfering the reference beam and the return beam to generate an interference pattern for detection by the imaging device.

In some embodiments the method may further comprise focusing the sample beam onto a surface of the substance. In other embodiments, the input beam may comprise type A and type B polarized light and the method may further comprise dividing the type A polarized light of the input beam into the reference beam and the type B polarized light of the input beam into the sample beam. In further embodiments, the method may additional comprise transforming the return beam into type A polarized light that may be reflected to prevent interference with the input beam.

BRIEF DESCRIPTION OF THE DRAWINGS

For a better understanding of embodiments of the system and methods described herein, and to show more clearly how they may be carried into effect, reference will be made by way of example, to the accompanying drawings in which:

FIG. 7 shows an alternative embodiment of a confocal imaging system implemented with two axicon lenses using a fiber optic cable.

DETAILED DESCRIPTION

Figure 1:
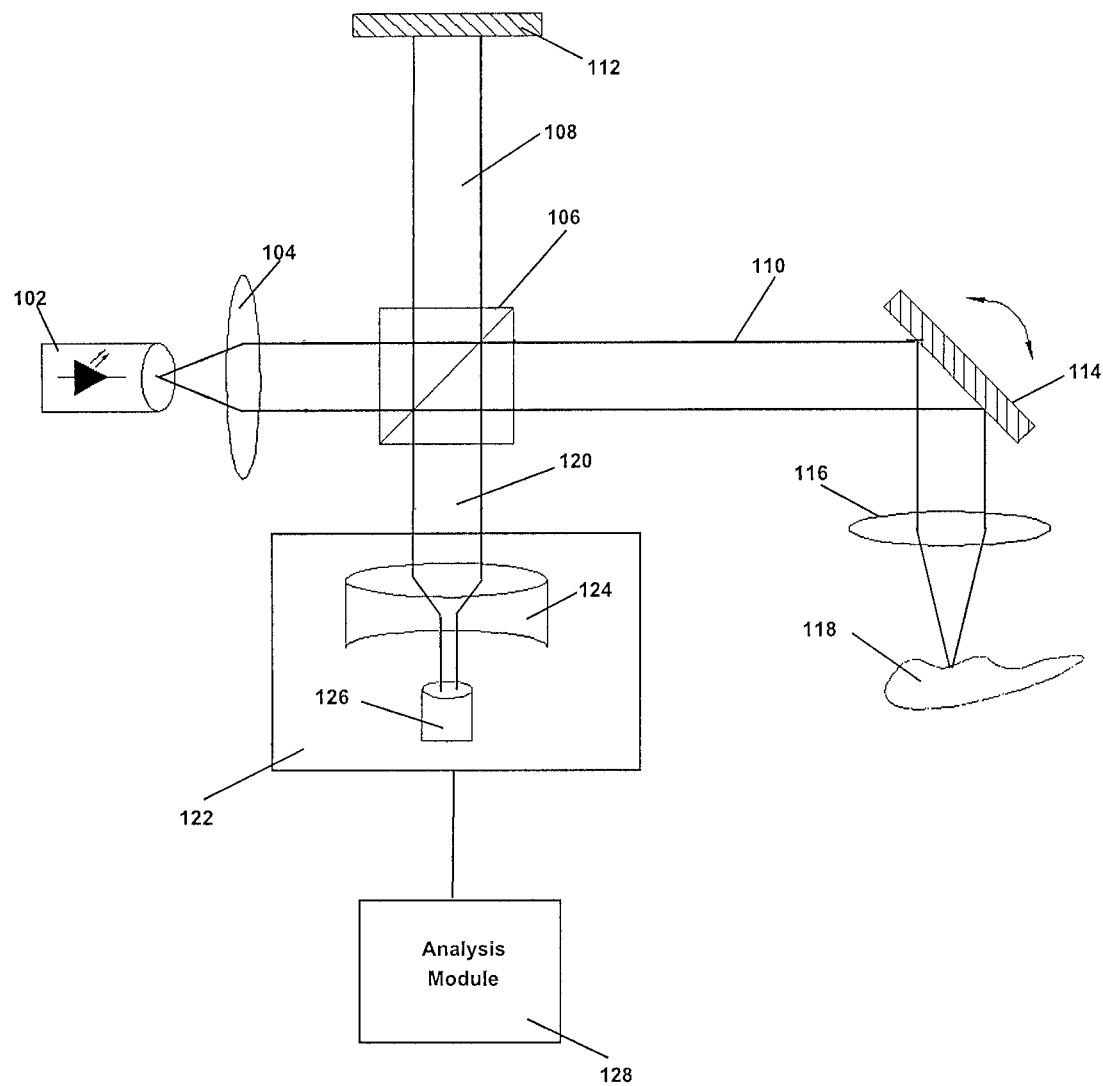
FIG. 1 shows an embodiment of a typical OCT system.

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

For the purpose of understanding signal losses in typical OCT systems, FIG. 1 shows an embodiment of OCT system 100. Low coherence light source 102 is collimated by collimating lens 104, producing a parallel beam of light, that is projected onto beam splitter 106.

Beam splitters are used split beams of light, a portion of the beam of light being reflected in the beam splitter and the remaining portion of the beam of light transmitting through the beam splitting splitter. Beam splitters can have various splitting ratios, some splitters reflecting 50% of a signal and transmitting the remaining 50% of the signal, while other beam splitters can operate at 90%/10% and others at splits of 99%/1%. Skilled persons will appreciate that different beam splitters can operate at different split ratios.

Beam splitter 106 splits the collimated beam into reference beam 108 and sample beam 110, reference beam 108 directed toward reference mirror 112 and sample beam 110 directed toward reflective surface 114.

Sample beam 110 is reflected off reflective surface 114 and focused by focusing lens 116 onto substance 118. This focused beam is then reflected or scattered back off a surface, or surfaces of substance 118 towards focusing lens 116 which collimates the reflected or scattered beam, and projects the beam towards reflective surface 114. Reflective surface 114 reflects the beam back towards beam splitter 106.

Reference beam 108, after being generated by beam splitter 106, is directed to reference mirror 112 and reflected back towards beam splitter 106. Beam splitter 106 then makes additional splits of both the reflection of reference beam 108 and the return of sample beam 110. In one such split, output beam 120 is formed reflecting a portion of the return of sample beam 110 and transmitting a portion of reference beam 108, these portions interfering to form output beam 120. Output beam 120 can project an interference pattern onto detector 122, which, in the embodiment shown, has beam reducer 124 and photo detector 126. The projected interference pattern can be analyzed by analysis module 128 to determine the structure of substance 118, for example the depth of various surface layers of substance 118.

The beam splitter additionally reflects the remaining portion of reference beam 108 and transmits the remaining portion of sample beam 110 back towards light source 102. This results in signal losses, the interference beam being generated by these portions interfering with the input beam. The embodiment shown in FIG. 1 shows a beam splitter operating with a 50%/50% split ratio, resulting in an output beam with a 50% signal loss, compared with the signal intensity of input source 102.

Confocal systems, such as confocal microscope systems use beam splitters as optical components and suffer similar signal losses.

Bypassing optical components that produce these signal losses, such as a beam splitter can reduce such signal losses. Using axicon lenses in OCT and confocal microscope systems can avoid losses created by beam splitters. Axicon lenses can be used to bypass beam splitters, or other optical components within an OCT confocal microscope system to increase the resulting signal intensity of the output beam.

Axicon lenses (sometimes referred to as conical lenses) are circularly symmetric optical elements that refract light by receiving a collimated solid circular light beam and outputting diverging ring or doughnut shaped light beam. Skilled persons will understand that reciprocal lens properties hold with axicon lenses, meaning that if the direction of light through the lens is reversed, it will make no difference of the effect on either side of the lens element. For example, in a positive lens with reciprocal properties a collimated light beam entering the lens will exit the lens converging to a single point, and light diverging towards the lens from a single point will exit the lens as a collimated light beam.

Figure 2:
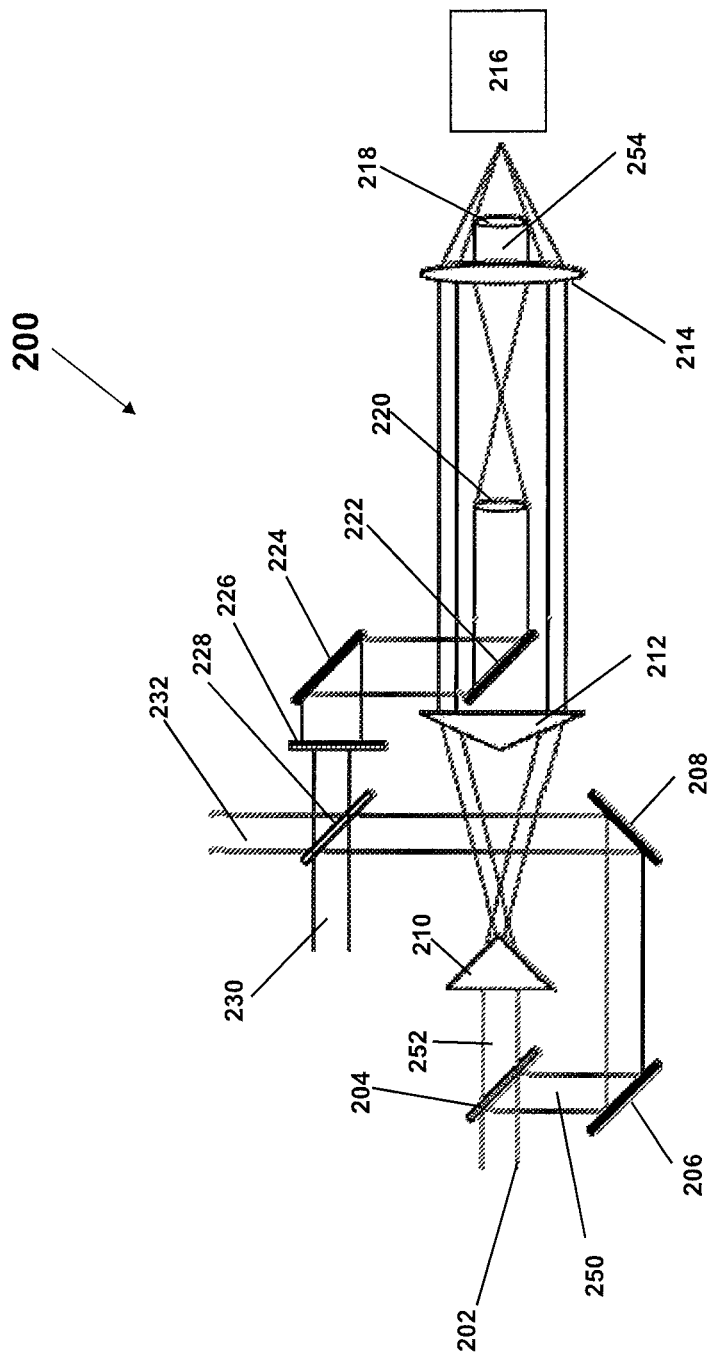
FIG. 2 shows an embodiment of an OCT system implemented with two axicon lenses.

With reference to FIG. 2, OCT system 200 is shown having two axicon lenses 210 and 212 where sample beam 252 is ultimately projected onto substance 216. Input beam 202, a collimated beam that can be collimated using a collimating lens or convex mirror, is received by OCT system 200, and is split by beam splitter 204, forming reference beam 250 and sample beam 252. Reference beam 250 can be directed to reflective surface 206, which in turn, reflects reference beam 250 towards beam splitter 228.

Sample beam 252 can be directed towards first axicon lens 210 and exits first axicon lens 210 as a diverging ring beam. The diverging ring beam is received by second axicon lens 212 which collimates the diverging ring beam into a collimated ring beam. First axicon lens 210 and second axicon lens 212 can be sized so that the collimated ring beam exiting second axicon lens 212 has an inner diameter sized so that there is no interaction or interference between the collimated ring beam and reflective surface 222 or collimating lens 220. This allows the collimated light beam to bypass reflective surface 222 and collimating lens 222 to reduce signal intensity losses of sample beam 252 projected onto substance 216. Additionally, the inner diameter of the collimated ring beam is larger than the diameter of return beam 254 exiting collimating lens 218, at any position along return beam 254, so that no portion of sample beam 252 interferes return beam 254.

The collimated ring beam is directed toward focusing lens 214 where it is focused onto substance 216 striking and/or penetrating one or more surfaces of substance 216. This produces a reflected or scattered beam off substance 216. The reflected or scattered beam is substantially conical in shape and is directed toward collimating lens 218. Collimating lens 218 collimates the reflected or scattered beam and generates return beam 254. Return beam 254 is directed back to focusing lens 214, where return beam 254 is focused and directed toward collimating lens 220. Collimating lens 220 can be sized and positioned so that no portion of collimating lens 220 and no portion of return beam 254 interferes or interacts with the collimated ring beam exiting second axicon lens 212. This sizing and positioning can reduce interference between collimated ring beam and return beam 254.

Return beam 254, after exiting collimating lens 220, is directed towards reflective surface 222, which directs return beam 254 to reflective surface 224. Reflective surface 222 can be sized so that it reflects the entirety of return beam 254, and additionally sized such that no portion of reflective surface 222 interferes with the collimated ring beam exiting axicon lens 212. This sizing of reflective surface 222 can reduce the degree of loss of sample beam 252 ultimately projected onto substance 216, can reduce signal intensity losses in return beam 254 ultimately interfering with reference beam 250 to generate output beams 230 and 232 (described below), and additionally can reduce signal losses by capturing the entirety of return beam 254 and bypassing beam splitter 228.

Reflective surface 222 projects return beam 254 onto reflective surface 224 which in turn projects return beam 254 onto mask 226. Mask 226 has an opening therethough, the opening being substantially the same size and substantially the same shape as the reflected portion of reference beam 250 directed towards beam splitter 228. This sizing of the opening can increase the quality of the interference patterns projected by output beams 230 and 232.

The return beam is reduced in diameter by the opening through mask 226 to have substantially the same diameter as reference beam 250, and is projected toward beam splitter 228. Beam splitter 228 receives return beam 254 and reference beam 250. Beam splitter 228 generates output beams 230 and 232, which are interference beams generated by interfering portions of return beam 254 and reference beam 250. A portion of return beam 254 is reflected by beam splitter 228 and interferes with the portion of reference beam 250 transmitted through beam splitter 228 to generate output beam 232. The other portion of return beam 254 is transmitted through beam splitter 228 and interferes with the other portion of reference beam 250 reflected by beam splitter 228, to generate output beam 230.

Output beams 230 and 232 can be projected onto one or more interferometers, such as CCD sensors, each output beam 230 and 232 producing an interference pattern to be analyzed by the one or more interferometers to determine information about substance 216, such as the depth of various surfaces within substance 216. The total output signal of OCT system 200 is nearly 100% of the input signal, skilled persons recognizing that there can be small inherent losses in optical components, for example, due to imperfections.

Figure 3:
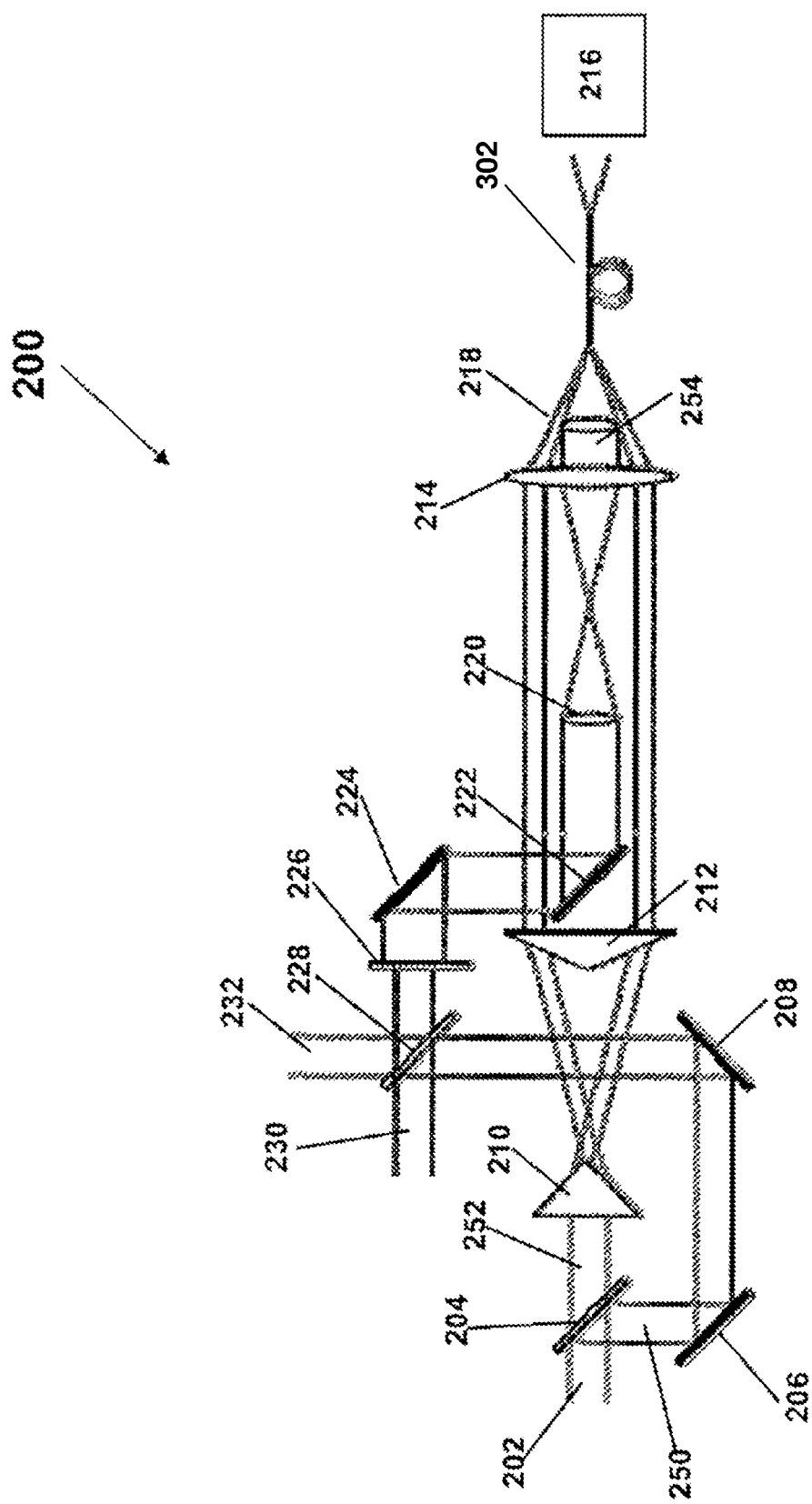
FIG. 3 shows an alternative embodiment of an OCT system implemented with two axicon lenses using a fiber optic cable.

With reference to FIG. 3, an alternative embodiment of the OCT system 200 is shown having fiber optic cable 302 positioned between focusing lens 214 and substance 216. In this embodiment, focusing lens 214 focuses the collimated ring beam exiting second axicon lens 212 to fiber optic cable 302. Fiber optic cable 302 can be positioned so that its exit point is directed toward substance 216 or in alternative embodiments, to an alternative light delivery system, the exiting beam projecting light onto substance 216. The exiting light is reflected or scattered off a surface, or surfaces, of substance 216, generating a reflected or scattered beam which is received by fiber optic cable 302 and returned to OCT system 200. The returned reflected or scattered beam is directed toward collimating lens 218 to generate return beam 254.

Figure 4:
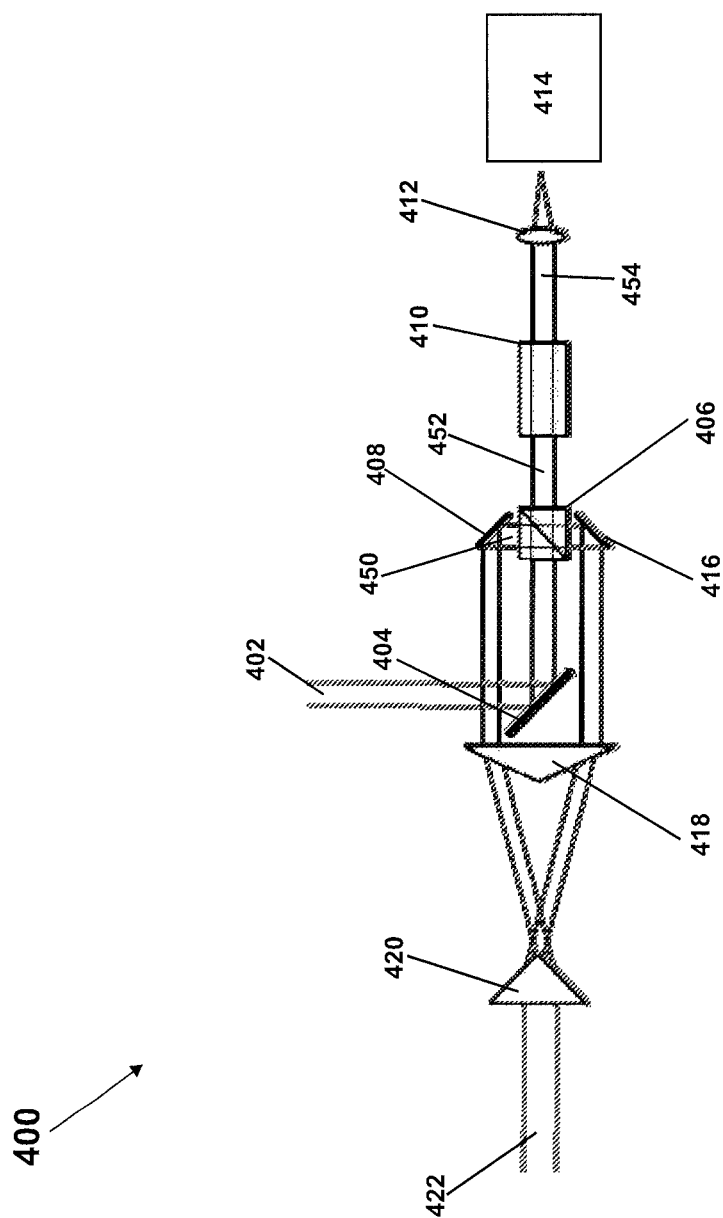
FIG. 4 shows an embodiment of an optical coherence tomography system implemented with two axicon lenses and polarization dependent optics.

With reference to FIG. 4, OCT system 400 is shown having two axicon lenses 418 and 420 and polarization dependent optics. Input beam 402, which is a collimated beam and can be collimated using a collimating lens or convex mirror, is received by OCT system 400. In this embodiment, input beam 402 is additionally a polarized beam made up of two types of polarized light (hereinafter referred to as type A and type B). Input beam 402 is directed toward reflective surface 404 which reflects input beam 402 towards beam splitter 406.

Beam splitter 406 is a polarization beam splitter of the type that reflects type A polarized light and transmits type B polarized light. Beam splitter 406 receives input beam 402 and reflects the type A polarized light component of input beam 402 toward reflective surface 408, this reflected type A polarized light forming reference beam 450.

The type B polarized light component of input beam 402 is transmitted through beam splitter 406 toward polarization element 410. This type B polarized light component forming sample beam 452. Sample beam 452 is passed through polarization element 410 and is focused by focusing lens 412 onto substance 414. The focused sample beam 452 strikes and/or penetrates one or more surfaces of substance 414, producing a reflected or scattered beam off substance 414. The reflected or scattered beam can be substantially conical in shape and is received by focusing lens 412 which produces return beam 454. Return beam 454 is received by focusing lens 412 from the non-focusing side which outputs a collimated beam, focusing lens having reciprocal properties.

The collimated return beam 454 then passes through polarization element 410 which transforms return beam 454 so that it is made up of type A polarized light. This type A polarized return beam 454 is received by beam splitter 406, which reflects substantially all of return beam 454, since, as discussed above, beam splitter 406 is the type that reflects type A polarized light and transmits type B polarized light.

Return beam 454 is reflected by beam splitter 406 toward reflective surface 416, reflecting off reflective surface 416 toward axicon lens 418. As discussed above, reference beam 450 is reflected off reflective surface 408 additionally, towards axicon lens 418. The optical components of OCT system 400 are positioned so that these two reflected beams directed off reflective surfaces 408 and 416 are sized and positioned so that the reflected beams bypass reflective surface 404 and so that these reflected beams strike axicon lens 418 at symmetrically opposite positions on axicon lens 418 relative to an axis bisecting the lens into two opposing halves. This positioning and arrangement reducing signal losses due to reference beam 450 and return beam 454 bypassing optical components that can otherwise interfere or interact with reference beam 450 or return beam 454, increasing the signal intensity value of output beam 422.

Axicon lens 418 redirects each of reference beam 450 and return beam 454 towards second axicon lens 420. The redirected beams exiting axicon lens 418 and travelling in a converging path to the position of second axicon lens 420 located where reference beam 450 interferes with return beam 454.

The interference beam produced by the interfering of reference beam 450 and return beam 454 that passes though second axicon lens 420 is collimated by second axicon lens 420, producing output beam 422. Output beam 422 is capable of projecting an interference pattern that can be received by an interferometer, such as a CCD sensor, for analysis to determine information about substance 414, such as the depth of various surface within substance 414. The total output signal intensity of OCT system 400 is nearly 100% of the input intensity signal, skilled persons recognizing that there can be small inherent losses in optical components, for example, due to imperfections in optical components.

Figure 5:
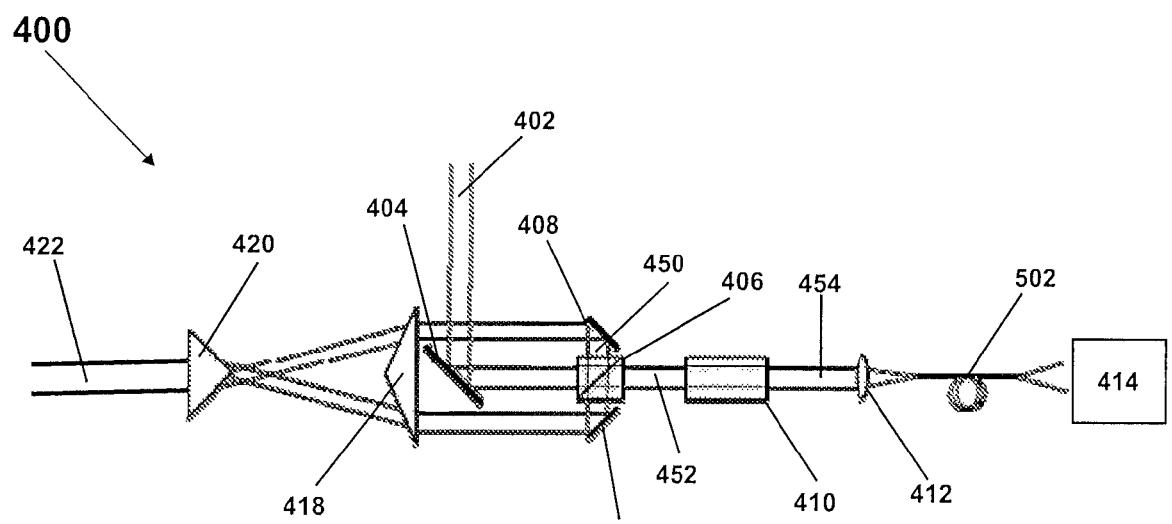
FIG. 5 shows an alternative embodiment of an optical coherence tomography system implemented with two axicon lenses and polarization dependent optics using a fiber optic cable.

With reference to FIG. 5, an alternative embodiment of OCT system 400 is shown having fiber optic cable 502 positioned between focusing lens 412 and substance 414. In this embodiment, focusing lens 412 focuses sample beam 452 to fiber optic cable 502. Fiber optic cable 502 can be positioned so that its exit point is directed toward substance 414 or, in some embodiments, into an alternative light delivery system for projecting light onto substance 414. The exiting light is reflected or scattered off a surface, or surfaces, of substance 414 generating a reflected or scattered beam which is received by fiber optic cable 502 and returned to OCT system 400. The returned reflected or scattered beam is then directed toward focusing lens 412, generating return beam 452.

Figure 6:
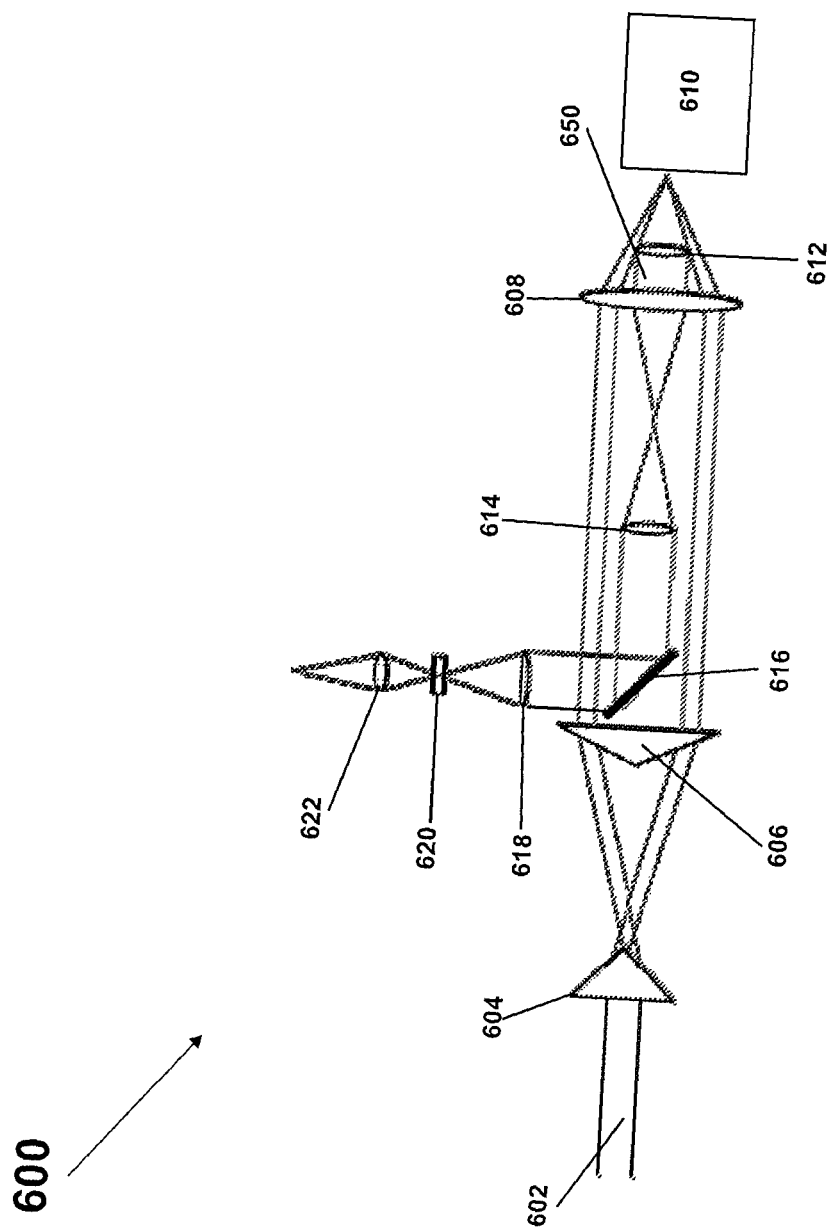
FIG. 6 shows an embodiment of a confocal imaging system implemented with two axicon lenses.

With reference to FIG. 6, confocal imaging system 600 is shown having two axicon lenses 604 and 606, where the sample beam projects onto substance 610. In the embodiment shown, axicon lenses 604 and 606 have replaced a beam splitter normally present in confocal imaging systems.

Confocal imaging system 600 receives input beam 602, which is a collimated beam and can be collimated using a collimating lens or convex mirror. Input beam 602 passing through axicon lens 604 and exiting axicon lens 604 as a diverging beam that is ring or doughnut shaped. The diverging ring beam is received by second axicon lens 606 which collimates the diverging ring beam into a collimated ring beam.

Axicon lens 604 and second axicon lens 606 are sized and positioned so that the collimated ring beam exiting second axicon lens 606 has an inner diameter sized so that the collimated ring beam does not interact or interfere with reflective surface 616 and collimating lens 614, thereby bypassing these optical elements. Additionally, the inner diameter is larger than the diameter of sample beam 650 exiting collimating the lens, at any position along sample beam 650. This sizing and arrangement can reduce losses in the amount of the collimated ring beam generated from input beam 602 that is ultimately projected onto substance 610.

The collimated ring beam is received by focusing lens 608, where it is focused onto substance 610, and contacts and/or penetrates one or more surfaces of substance 610. The focused beam is reflected or scattered off substance 610. The reflective or scattered beam being substantially conical in shape and directed towards collimating lens 612, which collimates the reflected or scattered beam to generate sample beam 650.

Sample beam 650 is directed back to focusing lens 608 where it is focused and directed to collimating lens 614, which substantially collimates sample beam 650. Sample beam 650, after being collimated by collimating lens 614 is projected onto reflective surface 616 which directs sample beam 650 toward focusing lens 618.

Collimating lens 614 and reflective surface 616 are sized and positioned so that no portions of collimating lens 614 and reflective surface 616 interfere with the collimated ring beam exiting the second axicon lens. This allows the collimated ring beam to bypass collimating lens 614 and reflective surface 616 to reduce the amount of losses of sample beam 650 projected onto substance 610. Additionally, collimating lens 614 and reflective surface 616 are sized and positioned to that no portion of sample beam 650 interacts or interferes with the collimated ring beam exiting second axicon lens 606.

Reflective surface 616 is sized to reflect the entirety of sample beam 650 toward focusing lens 618, bypassing axicon lens 606 and preventing portions of the sample beam from being directed away from the output of confocal imaging system 600, reducing signal losses.

Sample beam 650, when reflected off reflective surface 616, is directed toward focusing lens 618 which focuses sample beam 650 down into pin hole 620, resulting in the desired confocal imaging slice selection effect, meaning the out of plane light is discarded which gives an increase in resolution and a slice selection protocol where the slice thickness is proportional to the diameter of the pinhole. The sample beam 650 exits pin hole 620 as a diverging solid beam and is refocused by refocusing lens 622 and projected onto a detector device for analysis to determine the structure of substance 610, for example, for generating an image of substance 610.

The image generated of substance 610 can be detected and analyzed by a sensor and has a total output intensity signal of nearly 100% of the intensity of the input signal, skilled persons recognizing that there can be small inherent losses in optical components, for example, due to imperfections.

With reference to FIG. 7, an alternative embodiment of confocal imaging system 600 is shown having fiber optic cable 702 positioned between focusing lens 608 and substance 610. In this embodiment, focusing lens 608 focuses the collimated ring beam exiting second axicon lens 606 to fiber optic cable 702. Fiber optic cable 702 is positioned so that its exit point is directed toward substance 610, or in an alternative embodiment, a light delivery system to project the exiting light onto substance 610. The exiting light is reflected or scattered off a surface or surfaces of substance 610 generating a reflected or scattered beam, which is received by fiber optic cable 720 and returned to confocal imaging system 600. The returned or scattered beam is then directed toward collimating lens 612, generating sample beam 650.

The present invention has been described with regard to specific embodiments. However, it will be obvious to persons skilled in the art that a number of variants and modifications can be made without departing from the scope of the invention as described herein. For example, skilled persons will understand that alternative arrangement of optical elements in OCT and confocal microscope systems may produce substantially similar results when axicon lenses are used to bypass certain optical elements for providing improved signal intensity values of the output of such systems.

What is claimed is:

1. An interferometric optical device, comprising:
   a first beam splitter for splitting an input beam into a sample beam and a reference beam;
   a pair of axicon lenses through which the sample beam is directed, such that the sample beam forms a collimated ring beam;
   a focusing lens for focusing the collimated ring beam onto a sample or onto an optical fiber in optical communication with the sample;
   a first collimating lens for collecting scattered light from the sample and forming a return beam that passes through the focusing lens and is spatially separated from the sample beam, such that the return beam is coaxial within, and does not spatially overlap with, the collimated ring beam;
   one or more collimating and reflecting components located between the focusing lens and the first axicon lens, for collimating the return beam and for redirecting the return beam to prevent the return beam from interfering with the input beam, wherein the collimating and reflecting components are positioned such that the collimated ring beam bypasses the collimating and reflecting components; and
   a beam recombination means for interfering the reference beam and the return beam.

2. The interferometric optical device according to claim 1 wherein the collimating and reflecting components comprise a second collimating lens and a reflector.

3. The interferometric optical device according to claim 1 wherein one or more of the first beam splitter and the beam recombination means have a splitting ratio other than 50%/50%.

4. The interferometric optical device according to claim 1, further comprising a mask with an aperture therethrough for reducing the diameter of the return beam, the aperture having substantially the same size and substantially the same shape as the reflected portion of reference beam.

5. The interferometric optical device according to claim 1 wherein the reflector is configured to reflect the entirety of the return beam.

6. An optical coherence tomography system comprising the interferometric optical device according to claim 1.

7. A method of performing interferometry, comprising:
   directing an input beam into an interferometric device according to claim 1, such that the beam recombination means generates first and second interference beams from the reference beam and the return beam; and
   projecting one of the interference beams onto an optical sensor.

8. The method according to claim 7, further comprising projecting the other one of the interference beams onto an additional optical sensor.

9. An optical apparatus comprising:
   a pair of axicon lenses through which an input beam is directed, such that the input beam forms a collimated ring beam;
   a focusing lens for focusing the collimated ring beam onto a sample or onto an optical fiber in optical communication with the sample;
   a first collimating lens for collecting scattered light from the sample and forming a return beam that passes through the focusing lens and is spatially separated from the sample beam, such that the return beam is coaxial within, and does not spatially overlap with, the collimated ring beam; and
   one or more collimating and reflecting components located between the focusing lens and the first axicon lens, for collimating the return beam and for redirecting the return beam to prevent the return beam from interfering with the input beam, wherein the collimating and reflecting components are positioned such that the collimated ring beam bypasses the collimating and reflecting components.

10. The optical apparatus according to claim 9 wherein the collimating and reflecting components comprise a second collimating lens and a reflector.

11. The optical apparatus according to claim 9 wherein the focusing lens is a first focusing lens, the optical apparatus further comprising:
   a second focusing lens positioned to focus the return beam after the return beam is redirected; and
   a pinhole positioned at the focal point produced by the second focusing lens.

12. A confocal imaging system comprising the optical apparatus according to claim 9.

13. An interferometric optical system comprising the optical apparatus according to claim 9.

14. An interferometric optical device, comprising:
   a first beam reflector for redirecting an input beam towards a polarizing beamsplitter, such that when the input beam comprises a first polarization state and a second polarization state, a sample beam having the first polarization state is transmitted through the polarizing beamsplitter, and a reference beam having the second polarization state is reflected in a first direction by the polarizing beamsplitter;
   a focusing element for focusing the sample beam onto a sample or onto an optical fiber in optical communication with the sample, wherein the focusing element also collects and collimates scattered light from the sample, thereby forming a return beam;
   a polarization transforming element in optical communication with the focusing element and the polarizing beamsplitter, such that the return beam is incident on the polarizing beamsplitter in the second polarizing state, and such that the return beam is reflected by the polarizing beamsplitter in a second direction that is opposite to that of the first direction;
   a second beam reflector configured to receive the reference beam from the first direction and to reflect the reference beam;
   a third beam reflector configured to receive the return beam from the second direction and to reflect the return beam;
   wherein the reference beam and the return beam are reflected, respectively, by the second beam reflector and the third beam reflector, such that the return beam and the reference beam are parallel, and are spatially separated such that they bypass the first beam reflector; and
   a pair of axicon lenses configured to symmetrically receive, on opposite sides of an axis bisecting the pair of axicon lenses, the reference beam and the return beam, and to combine the reference beam and the return beam into an output beam.

15. An optical coherence tomography system comprising the interferometric optical device according to claim 14.

* * * * *